(12) United States Patent
Bridges

(10) Patent No.: US 7,191,500 B2
(45) Date of Patent: Mar. 20, 2007

(54) DISPOSABLE NONWOVEN UNDERGARMENTS

(75) Inventor: Cliff Bridges, Greensboro, NC (US)

(73) Assignee: Polymer Group, Inc., Charlotte, NC (US)

( * ) Notice: Subject to any disclaimer, the term of this patent is extended or adjusted under 35 U.S.C. 154(b) by 605 days.

(21) Appl. No.: 10/289,553

(22) Filed: Nov. 7, 2002

(65) Prior Publication Data

US 2003/0088955 A1 May 15, 2003

Related U.S. Application Data

(60) Provisional application No. 60/345,314, filed on Nov. 9, 2001.

(51) Int. Cl.
*D04H 5/02* (2006.01)

(52) U.S. Cl. .......................................... 28/104; 156/148

(58) Field of Classification Search .................. 28/104, 28/105, 167, 153, 103; 156/148, 163, 164, 156/309.6; 442/408, 684, 687; 604/358, 604/374, 375, 383, 365, 366
See application file for complete search history.

(56) References Cited

U.S. PATENT DOCUMENTS

| | | | |
|---|---|---|---|
| 3,485,706 A | 12/1969 | Evans | |
| 4,646,362 A * | 3/1987 | Heran et al. .................... | 2/400 |
| 4,674,135 A * | 6/1987 | Greene ........................... | 2/400 |
| 4,938,753 A * | 7/1990 | Van Gompel et al. | 604/385.29 |
| 5,093,190 A | 3/1992 | Kwok et al. | |
| 5,098,764 A | 3/1992 | Bassett et al. | |
| 5,103,501 A | 4/1992 | Meisels | |
| 5,244,711 A | 9/1993 | Drelich et al. | |
| 5,413,849 A * | 5/1995 | Austin et al. ................ | 442/329 |
| 5,516,572 A | 5/1996 | Roe | |
| 5,624,422 A | 4/1997 | Allen | |
| 5,766,746 A * | 6/1998 | Kampl et al. ................ | 428/219 |
| 5,822,823 A | 10/1998 | Polzin et al. | |
| 5,827,597 A | 10/1998 | James et al. | |
| 5,895,623 A * | 4/1999 | Trokhan et al. ................ | 28/104 |
| 6,022,818 A * | 2/2000 | Welchel et al. ............. | 442/384 |
| H1969 H | 6/2001 | Fell et al. | |
| 6,260,211 B1 | 7/2001 | Rajala et al. | |
| 6,270,623 B1* | 8/2001 | Goda et al. .................. | 162/114 |
| 6,289,519 B1 | 9/2001 | Murakami et al. | |
| 6,307,120 B1 | 10/2001 | Glaug | |
| 6,430,788 B1* | 8/2002 | Putnam et al. ................. | 28/104 |
| 2002/0034914 A1* | 3/2002 | De Leon et al. ............ | 442/384 |
| 2003/0009862 A1* | 1/2003 | Black et al. .................. | 28/104 |
| 2003/0087575 A1* | 5/2003 | Carlson et al. ............. | 442/408 |

* cited by examiner

*Primary Examiner*—A. Vanatta
(74) *Attorney, Agent, or Firm*—Wood, Phillips, Katz, Clark & Mortimer

(57) ABSTRACT

The present invention relates to a soft feeling, aesthetically pleasing, and form-fitting disposable nonwoven undergarment for men, women, and youths, and optionally comprises a protective panel for those individuals with mild incontinence conditions. It is the object of the present invention to provide a comfortable, durable disposable undergarment by forming the undergarment of a three-dimensionally imaged nonwoven fabric. The present invention discloses an assortment of durable, disposable undergarments capable of meeting the needs of the general public, and specifically, to subsets of the population such as travelers, athletes, medical personnel and patients, for which routine care of conventional undergarments is inconvenient or unavailable.

21 Claims, 4 Drawing Sheets

DISPOSABLE NONWOVEN UNDERGARMENTS

TECHNICAL BACKGROUND

The present invention relates to a soft feeling, aesthetically pleasing, and form-fitting disposable nonwoven undergarment for men, women, and youths, and optionally comprises a protective panel for those individuals with mild incontinence conditions.

BACKGROUND OF THE INVENTION

Undergarments are those garments that come into direct contact with the skin. They are usually worn under an outer layer of clothing and remain generally unseen by the public. Undergarments cover a variety of constructs such as basic, woven, cotton undershirts and underpants for daily wear, absorbent disposable undergarments such as diapers and incontinence devices used to absorb and retain liquid waste, as well as specialty undergarments such as travel wear, medical wear, and athletic wear.

Disposable undergarments are widely accepted due to the convenience of use, however, such undergarments are often cumbersome, uncomfortable, noisy, and aesthetically unappealing. Prior art discloses disposable undergarments for incontinence purposes, traveling convenience, fem-care products, and medical wear.

Glaug, U.S. Pat. No. 6,307,120 discloses an absorbent incontinence article whereby the absorbent incontinence article is a cloth-like, breathable, disposable, brief comprising plural fastening tapes.

Fell, et al, H1, 969 discloses an absorbent disposable undergarment that utilizes a breathable microporous film as a backing member to improve absorbent and containment characteristics, as well as, to improve comfort for garments such as incontinence devices.

Meisels, U.S. Pat. No. 5,103,501 discloses three articles of disposable underwear for use during travel. The undershirt, men's underpants, and women's underpants, contain magnetic fasteners in order to minimize the amount of dressing time necessary with use of these garments and prevent tearing of the garment during removal.

Greene, U.S. Pat. No. 4,674,135 discloses a durable disposable undergarment that is made of nonwoven cellulosic paper or paper-like material, in which the garment is intended for use by travelers. The disposable garment includes a small bag to be used upon disposal of the garment.

Rajala, et al., U.S. Pat. No. 6,260,211 discloses a disposable undergarment that provides back-up protection for women in the event that a sanitary napkin should leak.

Murakami, et al., U.S. Pat. No. 6,289,519 discloses a disposable, Atrunk-type@, undergarment constructed of a spunbond nonwoven, whereby the trunks are intended for use by medical team members such as doctors and nurses, as well as patients.

Prior art lacks a durable, disposable, nonwoven undergarment that is suitable for daily use. The majority of disposable undergarments is directed toward diapers and incontinence devices or fails to provide the comfort necessary for daily use. Further, for those individuals suffering from a mild incontinence condition, the only available undergarment suitable for use are those of a diaper-like construction, which exhibit a negative aesthetic appeal. In addition, available incontinence devices are designed to withstand a high volume of liquid, which makes the traditional, diaper-like, incontinence device too burdensome. Previously mentioned disposable undergarments are either noisy or contain unpleasant fasteners.

It is the object of the present invention to provide a soft feeling, aesthetically pleasing, and form-fitting disposable undergarment that offers the wearer reassuring comfort. The present invention is durable and intended for daily use, but is also useful in disposable athletic, travel, or medical undergarment, and when so constructed, as a disposable undergarment for mild incontinence conditions.

SUMMARY OF THE INVENTION

The present invention relates to a soft feeling, aesthetically pleasing, and form-fitting disposable nonwoven undergarment for men, women, and youths, and optionally comprises a protective panel for those individuals with mild incontinence conditions.

Most disposable undergarments currently available are awkward, noisy, or comprise unpleasant fasteners. It is the object of the present invention to provide a comfortable, durable disposable undergarment by forming the undergarment of a three-dimensionally imaged nonwoven fabric.

Nonwoven fabrics can be comprised of natural or synthetic fiber, or a combination thereof, which are formed into a web or batt and then bonded or interlocked by means commonly known to one skilled in the art.

Nonwoven fabrics can be processed to exhibit suitable hand, drapeability, and three-dimensional image or pattern to provide for a comfortably fitting, fashionable, disposable undergarment. The present invention discloses an assortment of durable, disposable undergarments capable of meeting the needs of the general public, and specifically, to subsets of the population such as travelers, athletes, medical personnel and patients, for which routine care of conventional undergarments is inconvenient or unavailable.

Individuals with a mild incontinence condition, who require a device suitable for limited urinary containment, may also benefit from an undergarment made in accordance with the present invention. Currently available incontinence undergarments are bulky, and usually resemble the construct of a diaper. The disposable nonwoven undergarment for mild incontinence conditions of the present invention is trim, form fitting, and is equipped with a moisture management panel. In addition, the undergarment is fashionable and comfortable.

DETAILED DESCRIPTION OF THE INVENTION

While the present invention is susceptible of embodiment in various forms, hereinafter is described presently preferred embodiments of the invention, with the understanding that the present disclosure is to be considered as exemplifications of the invention, and is not intended to limit the invention to the specific embodiments illustrated.

The nonwoven fabric of the present invention is formed from natural fibers, synthetic fibers, or a combination of natural and synthetic fibers. The fibers may be of finite staple length, continuous filaments and the blends thereof. Synthetic fibers may be selected from thermoset polymers such as polyacrylates, or from thermoplastic polymers, including; polyamides, polyesters, or polyolefins, such as polypropylene or polyethylene, their derivatives, and combinations thereof. The synthetic fibers of the present invention may also include any fibers with multi-component configurations, such as side-by-side or sheath-core, as well as geometric variations. The natural fibers of the present invention are cellulosic in nature such as cotton, wood pulp, or rayon.

The nonwoven fabric used in accordance with the present invention should be durable and able to withstand the stress of continual body movement involved with everyday activities. The fabric should also have suitable drape and hand properties so that the fabric will conform to the curves of the body. In addition, the fabric should have a hydrophilic and hydrophobic sides in order absorb and repel moisture where needed.

Figure 1:
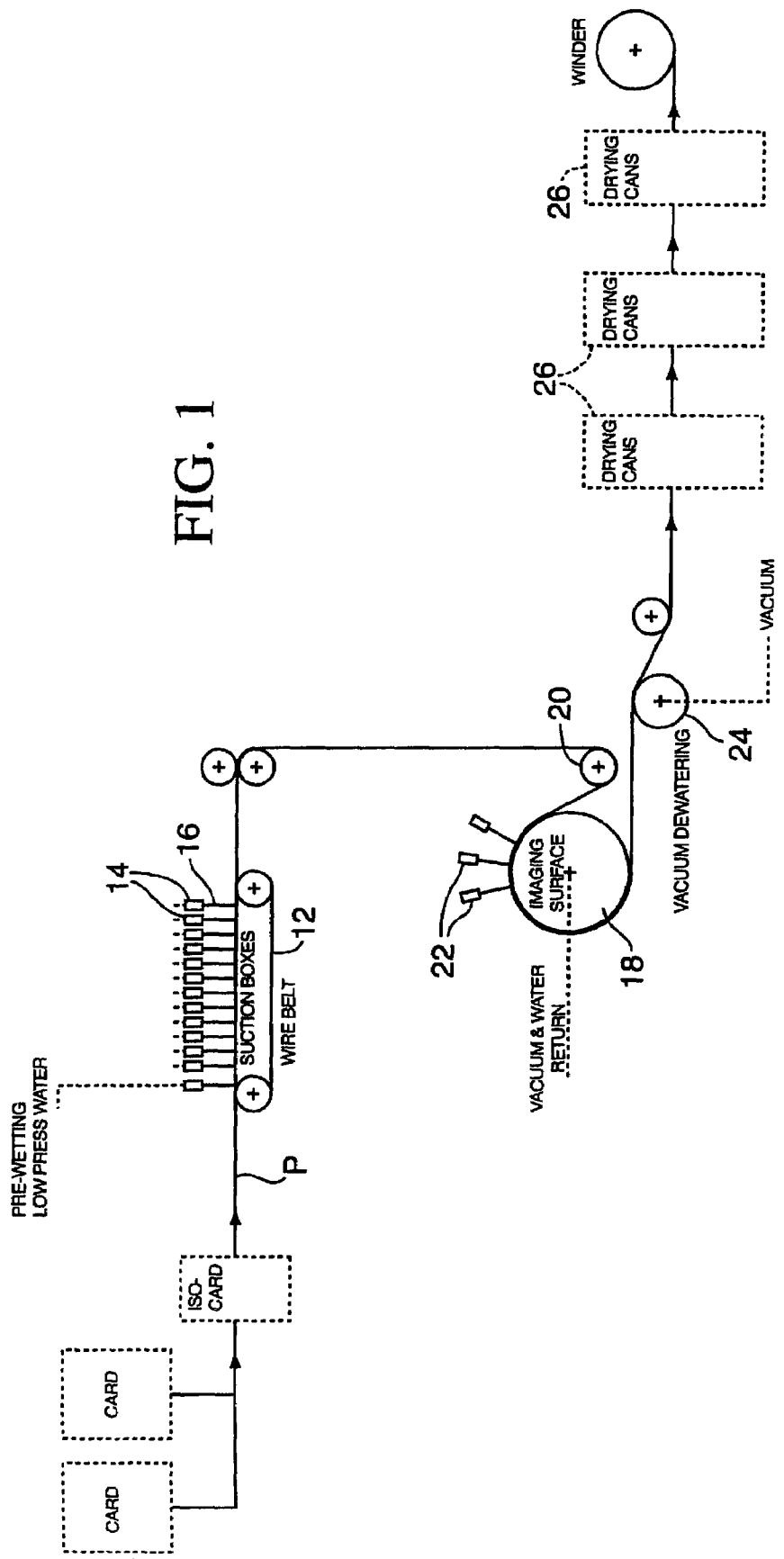
FIG. 1 is a depiction of the apparatus for the fabrication of the nonwoven fabric according to the present invention.
Figure 3:
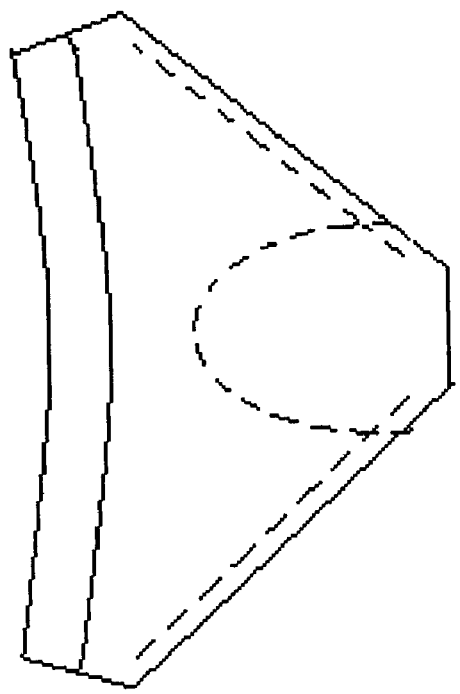
FIG. 3 is a perspective view of a male bikini style disposable undergarment according to the present invention.
Figure 2:
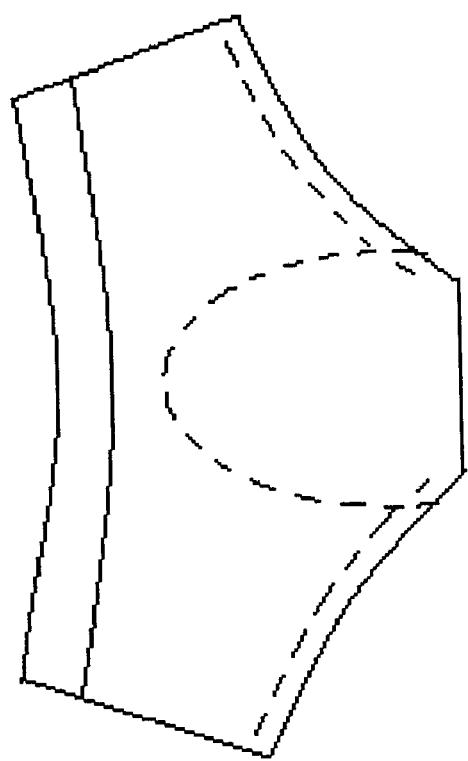
FIG. 2 is a perspective view of a male brief style disposable undergarment according to the present invention.
Figure 5:
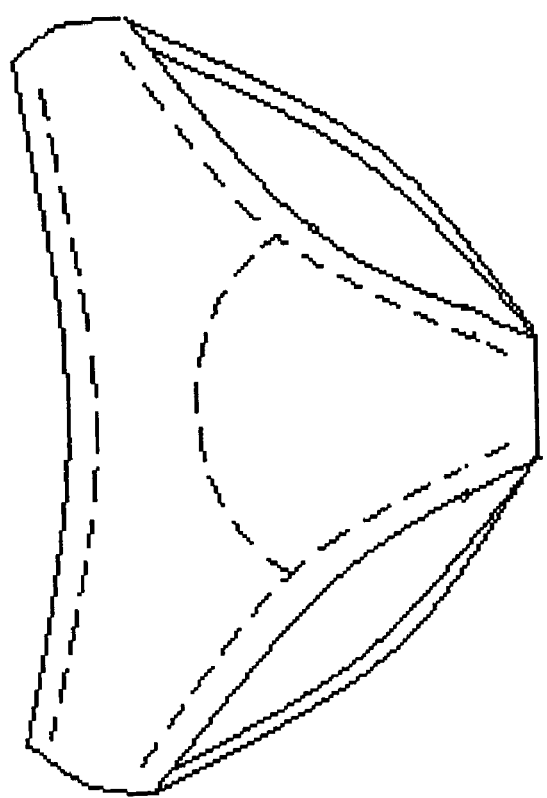
FIG. 5 is a perspective view of a female bikini style disposable undergarment according to the present invention.
Figure 4:
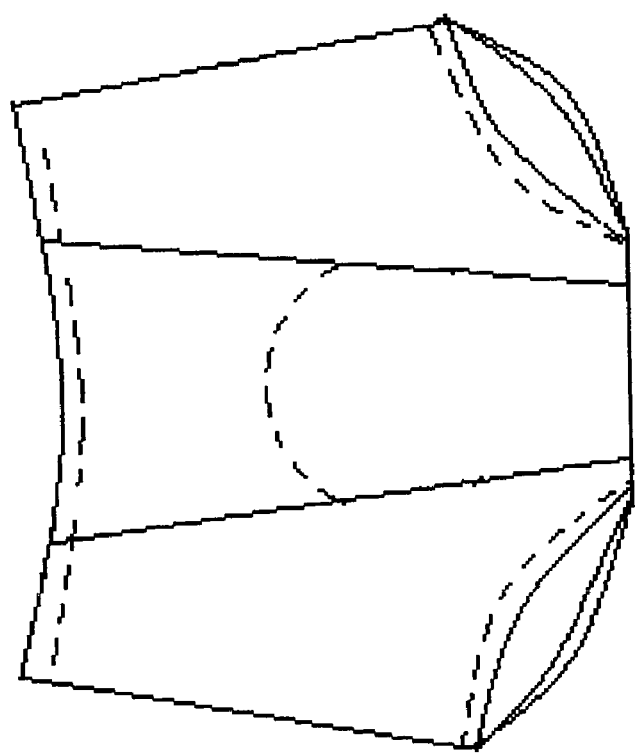
FIG. 4 is a perspective view of a female brief style disposable undergarment according to the present invention.
Figure 7:
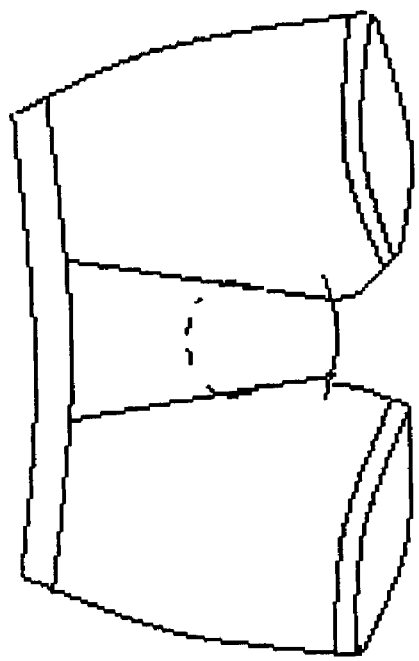
FIGS. 6 and 7 are perspective views of a male sport brief style disposable undergarment according to the present invention.
Figure 6:
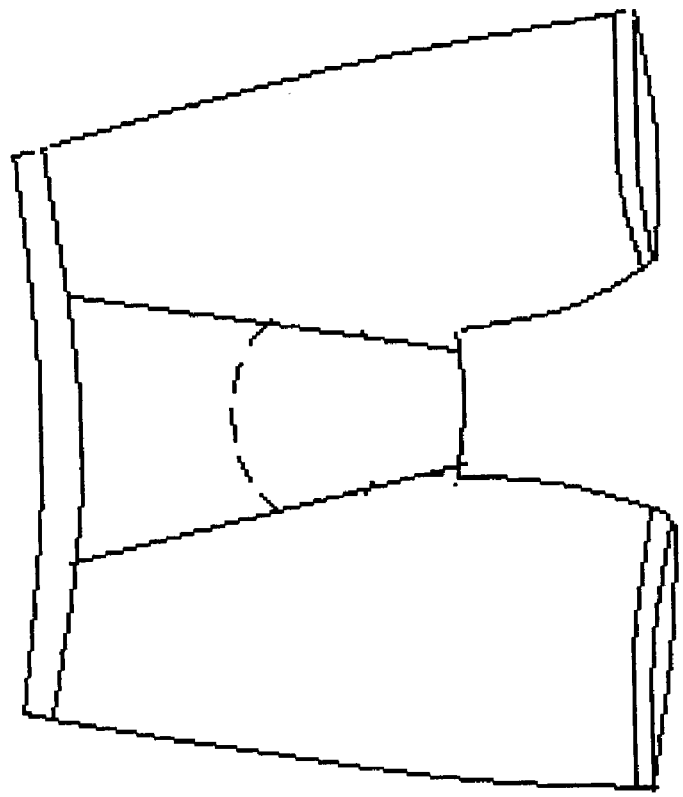

In reference to FIG. 1, therein is illustrated an apparatus for practicing the method of the present invention for forming a nonwoven fabric. The fabric is formed from a fibrous matrix, which comprises fibers selected to promote economical manufacture, while achieving the desired resultant nonwoven fabric. The fibrous matrix is preferably carded and subsequently air-randomized to form a precursor web, designated P.

FIG. 1 illustrates a hydroentangling apparatus for forming nonwoven fabrics in accordance with the present invention. The apparatus includes a foraminous forming surface in the form of a flat bed entangler 12 upon which the precursor web P is positioned for pre-entangling. Precursor web P is then sequentially passed under entangling manifolds 14, whereby the precursor web is subjected to high-pressure water jets 16. This process is well known to those skilled in the art and is generally taught by U.S. Pat. No. 3,485,706, to Evans, hereby incorporated by reference.

The entangling apparatus of FIG. 1 further includes an imaging and patterning drum 18 comprising a three-dimensional image transfer device for effecting imaging and patterning of the now-entangled precursor web. After pre-entangling, the precursor web is trained over a guide roller 20 and directed to the image transfer device 18, where a three-dimensional image is imparted into the fabric on the foraminous forming surface of the device. The web of fibers is juxtaposed to the image transfer device 18, and high pressure water from manifolds 22 is directed against the outwardly facing surface from jet spaced radially outwardly of the image transfer device 18. The image transfer device 18, and manifolds 22, may be formed and operated in accordance with the teachings of commonly assigned U.S. Pat. No. 4,098,764, U.S. Pat. No. 5,244,711, U.S. Pat. No. 5,822,823, and U.S. Pat. No. 5,827,597, the disclosures of which are hereby incorporated by reference. It is presently preferred that the precursor web P be given a three-dimensional image suitable to provide fluid management, as will be further described, to promote use of the present nonwoven fabric in disposable absorbent articles. The entangled fabric can be vacuum dewatered at 24, and dries at an elevated temperature on drying cans 26.

The nonwoven fabric of the present invention may be a composite, laminate, single layer or multiple layers so as to incorporate a support member, such as a scrim and/or absorbent mechanisms, suited for limited urinary containment, into the undergarment. The nonwoven may be imaged, such as with ribs or swirls, etc., aperatured, or modified aesthetically through subsequent dyeing, and printing, or by using colored fibers during the manufacturing step, to achieve the affects of the desired nonwoven disposable undergarment. The nonwoven fabric has a preferred basis weight range of 1.5–5.5 ounces per square yard, with a range of 2.0–3.0 ounces per square yard being most preferred.

A disposable nonwoven undergarment has skin health and hygiene benefits. The breathable and moisture absorbing characteristics of the nonwoven fabric utilized in the disposable undergarment provides the skin with a comfortable environment. The nonwoven fabric helps keep the skin oxygenated and dry, which is beneficial for those individuals with an active lifestyle.

The nonwoven disposable undergarment is typically of the representative Abrief@ design, wherein the undergarment is specific to gender and end use application. The brief of the present invention may be scaled to various sizes, i.e. small, medium, large, etc, in order to accommodate various body types or forms. In general, the undergarment is comprised of one or more pieces that are preferentially thermally welded, mechanically stitched, or adhesively bonded at the seams. Each undergarment comprises a waist opening at the upper portion of the undergarment and a pair of leg openings at the lower portion of the undergarment. The undergarment may optionally contain an elastic portion around the waist and leg openings.

In one embodiment, the disposable undergarment comprises a front panel and a back panel, with an interconnecting crotch region, wherein said front, back panel, and an interconnecting crotch region are mechanically secured together at their transverse edges (i.e., the front and back panels are joined to each other at opposite side seams, and the crotch regions of each panel are joined at a bottom seam). Alternatively, the garment may be unitary in construction, having a generally hourglass-shape, with the front and back panel integrally joined with n interconnecting crotch region. The garment is formed by joining the front and back panel to each other at opposite side seams. The nonwoven undergarment contains two elasticized leg openings and an elasticized waist. The imaged nonwoven undergarment consists of 50% polyester and 50% rayon, whereby the nonwoven fabric is of a layered construct, wherein the soft, hydrophilic rayon fabric layer is inside the undergarment against the skin while the hydrophobic, polyester fabric makes up the facing of the undergarment. The disposable undergarment of this embodiment also contains a discrete cellulosic protective panel for moisture management.

It is within the purview of the present invention to provide medical personnel and patients, male and female athletes, individuals that travel, and individuals with mild incontinence conditions with a comfortable, yet durable nonwoven disposable undergarment. Each disposable undergarment being tailored to the needs of these individuals, but all them having in common a soft feeling, aesthetically pleasing, form-fitting quality that is currently unavailable in disposable undergarments.

What is claimed is:

1. A process for fabricating a disposable nonwoven undergarment comprising:
   a. providing a precursor nonwoven web comprising a hydrophobic side and a hydrophillic side;
   b. providing a foraminous surface;
   c. hydroentangling said precursor web on said foraminous surface to form a patterned and imaged nonwoven fabric comprising imparting only three-dimensional, aperture-free images into the precursor web;
   d. optionally dyeing said patterned and imaged nonwoven fabric;
   e. forming said patterned and imaged nonwoven fabric into a front panel, a back panel, and crotch region; and
   f. joining said front panel, back panel, and crotch region at seams to form a disposable undergarment.

2. A process for fabricating a disposable nonwoven undergarment as in claim 1, wherein said precursor web is a fibrous blend of synthetic and natural fibers.

3. A process for fabricating a disposable nonwoven undergarment as in claim 2, wherein said synthetic fibers are selected from the group consisting of: polyacrylates, polyamides, polyesters, polypropylene, polyethylene, and mixtures thereof, and derivatives thereof.

4. A process for fabricating a disposable nonwoven undergarment as in claim 3, wherein said synthetic fibers are polyester.

5. A process for fabricating a disposable nonwoven undergarment as in claim 2, wherein said natural fibers are selected from the group consisting of: cotton, wood pulp, rayon, and mixtures thereof.

6. A process for fabricating a disposable nonwoven undergarment as in claim 5, wherein said natural fibers are rayon.

7. A process for fabricating a disposable nonwoven undergarment as in claim 1, wherein said foraminous surface is a three-dimensional image transfer device.

8. A process for fabricating a disposable nonwoven undergarment as in claim 1, wherein said disposable nonwoven undergarment is imparted with a pattern or three-dimensional image, by means of a three-dimensional image transfer device.

9. A process for fabricating a disposable nonwoven undergarment as in claim 1, wherein said formed disposable nonwoven undergarment is comprised of one patterned or imaged nonwoven fabric piece.

10. A process for fabricating a disposable nonwoven undergarment as in claim 1, wherein said step of joining comprises a method selected from the group consisting of thermal welding, mechanical stitching, adhesive bonding, and mixtures thereof.

11. A process for fabricating a disposable nonwoven undergarment as in claim 10, wherein said step of joining comprises mechanical stitching.

12. A process for fabricating a disposable nonwoven undergarment as in claim 1, wherein said undergarment is for daily use.

13. A process for fabricating a disposable nonwoven undergarment as in claim 1, wherein said process further comprises providing a moisture absorbent panel in the crotch region to accommodate mild incontinence.

14. A process for fabricating a disposable nonwoven undergarment as in claim 1, wherein said process comprises providing elastically lined leg openings and waist opening.

15. A process for fabricating a disposable nonwoven undergarment in accordance with claim 1, wherein said front panel and said back panel are formed unitarily with said crotch region.

16. A process for fabricating a disposable nonwoven undergarment in accordance with claim 1, wherein said front panel and said back panel are formed separately and are joined to each other at said side seams, and at a bottom seam at said crotch region.

17. A process for fabricating a disposable nonwoven garment as in claim 1, wherein the precursor nonwoven web is 50% rayon and 50% polyester.

18. A process for fabricating a disposable nonwoven garment as in claim 17, wherein the hydrophobic side comprises polyester and the hydrophillic side comprises rayon.

19. A process for fabricating a disposable nonwoven garment as in claim 18, wherein the hydrophobic side faces away from the skin of an undergarment wearer, and the hydrophillic side is closest to the skin of the wearer.

20. A process for fabricating a disposable nonwoven garment as in claim 1, wherein the fibers are carded and air randomized to form the precursor web.

21. A process for fabricating a disposable nonwoven garment as in claim 1, wherein said undergarment does not require a fastener.

* * * * *